United States Patent
Latiolais

(10) Patent No.: US 10,279,114 B2
(45) Date of Patent: May 7, 2019

(54) SYRINGE FOR AND METHOD OF DELIVERING A VOLUME OF SOLUTION WITH GUIDANCE BEARING IN VIEW OF STANDARD AND NON-STANDARD CARPULES

(71) Applicant: Lon J. Latiolais, Georgetown, TX (US)

(72) Inventor: Lon J. Latiolais, Georgetown, TX (US)

(73) Assignee: VYLON IP HOLDING, LLC, Breaux Bridge, LA (US)

( * ) Notice: Subject to any disclaimer, the term of this patent is extended or adjusted under 35 U.S.C. 154(b) by 69 days.

(21) Appl. No.: 14/704,557

(22) Filed: May 5, 2015

(65) Prior Publication Data

US 2016/0158447 A1     Jun. 9, 2016

Related U.S. Application Data

(63) Continuation-in-part of application No. 14/563,702, filed on Dec. 8, 2014.

(51) Int. Cl.

| | |
|---|---|
| *A61J 1/06* | (2006.01) |
| *A61M 5/24* | (2006.01) |
| *A61M 5/31* | (2006.01) |
| *A61M 5/34* | (2006.01) |

(52) U.S. Cl.
CPC ............ *A61M 5/3129* (2013.01); *A61J 1/062* (2013.01); *A61M 5/347* (2013.01); *A61M 5/348* (2013.01);
(Continued)

(58) Field of Classification Search
CPC .... A61M 5/3129; A61M 5/347; A61M 5/348; A61M 5/349; A61M 2005/2407;
(Continued)

(56) References Cited

U.S. PATENT DOCUMENTS

| | | |
|---|---|---|
| 3,767,085 A | 10/1973 | Cannon et al. |
| 3,848,593 A | 11/1974 | Baldwin |

(Continued)

FOREIGN PATENT DOCUMENTS

| | | |
|---|---|---|
| EP | 2407194 A1 | 1/2012 |
| WO | 1997025932 A1 | 7/1997 |

OTHER PUBLICATIONS

Dental Products Report, Dec. 17, 2012, introduction of VibraJect from ITL Dental.

(Continued)

*Primary Examiner* — Lauren P Farrar

(57) ABSTRACT

Methods and apparatuses are disclosed with regard to syringe-transfer of a solution or other fluid, optionally with a guidance bearing, within a standard or non-standard carpule, optionally having sealed top ends and measurement gradations, i.e., indicia. One embodiment is a non-standard carpule barrel having a top portion, a bottom portion, and a barrel portion therebetween. The top portion includes an opening for receiving a syringe plunger and at least a first portion for connecting to an upper portion of the syringe. The bottom portion includes another opening capable of holding a bottom end of the carpule, wherein the carpule may be a standard carpule or a non-standard carpule. The barrel portion is located between the top portion and bottom portion, and includes a cradle, which has a length capable of holding a standard or a non-standard carpule, which has a greater width than a standard carpule.

17 Claims, 5 Drawing Sheets

(52) U.S. Cl.
CPC ..... *A61M 5/349* (2013.01); *A61M 2005/2407* (2013.01); *A61M 2005/2488* (2013.01); *A61M 2005/2492* (2013.01); *A61M 2005/3131* (2013.01); *A61M 2005/3139* (2013.01); *A61M 2005/3142* (2013.01)

(58) Field of Classification Search
CPC .. A61M 2005/2488; A61M 2005/2492; A61M 2005/3131; A61M 2005/3139; A61M 2005/3142; A61J 1/062
See application file for complete search history.

(56) References Cited

U.S. PATENT DOCUMENTS

| | | | |
|---|---|---|---|
| 4,758,234 A * | 7/1988 | Orentreich | A61M 5/24 604/232 |
| 4,919,657 A | 4/1990 | Haber et al. | |
| 5,137,528 A | 8/1992 | Crose | |
| 5,542,934 A | 8/1996 | Silver | |
| 5,603,695 A | 2/1997 | Erickson | |
| 6,312,413 B1 | 11/2001 | Jensen et al. | |
| 2002/0055720 A1 | 5/2002 | Hohlfelder et al. | |
| 2005/0101913 A1 | 5/2005 | Hohlfelder et al. | |
| 2007/0060875 A1 | 3/2007 | Bassarab et al. | |
| 2009/0182301 A1 | 7/2009 | Bassarab et al. | |
| 2012/0214124 A1 * | 8/2012 | McLelland | A61C 19/08 433/90 |
| 2013/0085447 A1 * | 4/2013 | Manke | A61M 5/31515 604/111 |

OTHER PUBLICATIONS

ProMed web page, May 9, 2013.
Septodont Inc. web page, May 9, 2013.

* cited by examiner

SYRINGE FOR AND METHOD OF DELIVERING A VOLUME OF SOLUTION WITH GUIDANCE BEARING IN VIEW OF STANDARD AND NON-STANDARD CARPULES

RELATED APPLICATION

This disclosure is a continuation-in-part of and both claims domestic priority to and the benefit of pending U.S. patent application Ser. No. 14/563,702 filed on Dec. 8, 2014, the entirety of which is incorporated herein by this reference.

FIELD OF DISCLOSURE

The disclosure relates, generally, to methods and apparatuses that permit delivery of a volume of a fluid, e.g., medicine, delivered through the use of a standard or non-standard carpule placed in and through use of a guidance bearing in a syringe.

BACKGROUND

In the medical field, a syringe is an apparatus or device that is a commonplace tool for injecting and delivering a fluid into a patient or withdrawing a fluid or material from a patient, e.g., human or non-human, for medical and/or preventative reasons. When delivering the fluid (e.g., a medicine comprising an anesthetic, an analgesic, or other fluid injected, infused and/or delivered for medical and/or preventative reasons), the syringe may be loaded with a standard carpule, which may contain the medicine or other fluid that reaches the patient by someone pushing downwardly on the syringe's plunger rod that terminates in a hook, which pierces the top of the standard carpule. After this piercing, the medicine or other fluid is pushed out of the syringe's needle by someone continuing to push downwardly on the syringe's plunger rod, so that the movable plug within the standard carpule moves down the standard carpule. Once the movable plug is at the bottom of the standard carpule, another standard carpule must be loaded into the syringe in order to provide the patient with additional medicine or other fluids. The changing and/or re-loading of multiple carpules into the syringe, in addition to the necessity for multiple injections for delivery of the medicine contained within the multiple carpules, creates health risks for physicians and patients, in addition to increasing the costs associated with materials, time, labor and other resources.

Apparatuses and methods for delivery or withdrawal of a volume of fluid greater than a standard carpule volume are desired and needed to reduce: (1) health risks associated with multiple injections (needle-sticks) and the use of multiple carpules; (2) costs associated with the manufacturing of multiple carpules; (3) costs associated with the use of the materials required for the manufacturing of multiple carpules; (4) excess time required in delivering or withdrawing multiple carpules because a volume of solution, greater than the volume held by a standard carpule, is needed; and (5) the emotional trauma experienced by patients having to receive multiple injections due to the need for multiple carpules.

SUMMARY

One example embodiment includes a method for transferring a fluid that comprises applying a force with a syringe plunger, wherein the applied force causes the syringe plunger to forcibly connect to a non-standard carpule loaded into a barrel of a syringe, wherein the non-standard carpule has a volume that is different from a standard carpule. The method may continue by moving a solution or other fluid through a syringe needle, which may be in fluid communication with the non-standard carpule, and adjusting the volume of the solution or other fluid in the non-standard carpule, subsequent to injecting or applying the force to the syringe plunger. In an embodiment, the barrel of the syringe may be removable from the syringe and interchangeable, such that the barrel may be a standard barrel or a non-standard barrel having a capability of holding different volumes of fluid.

In another example embodiment, the applied force to the syringe plunger may include pushing down on the syringe plunger to connect to a non-standard carpule, inserting the syringe plunger into the non-standard carpule, or combinations thereof. In an alternative, example embodiment, the applied force to the syringe plunger may include pulling upwards on the syringe plunger to at least partially fill the non-standard carpule with a fluid.

In yet another example embodiment, there is a method for delivering a solution or other fluid, wherein the method includes loading a non-standard carpule into a syringe having a non-standard carpule barrel, and wherein the non-standard carpule may have a volume that is different (e.g., greater or smaller) from a standard carpule. The syringe may further include a syringe plunger and syringe needle, and the method may include applying a force to the syringe plunger for pushing a volume of the solution or other fluid within the non-standard carpule towards the syringe needle. The method may further include emitting at least a portion of the volume of the solution, or other fluid, from the syringe needle that is in fluid communication with the non-standard carpule.

The syringe may include an upper portion and a bottom portion, and the upper portion of the syringe may be connected to a top portion of the non-standard carpule barrel, which may be removable or irremovable from the syringe. In an embodiment, the connecting of the top portion of the non-standard carpule barrel to the upper portion of the syringe may be removable, and the removable connection may include the use of threading, screwing, latching, snapping, or combinations thereof, for the removable connection. In an alternative embodiment, the connecting of the top portion of the non-standard carpule barrel to the upper portion of the syringe may be irremovable, and the irremovable connection may include the use of welding, bonding, fusing, or combinations thereof. In an embodiment, an interchangeable barrel may be connected to the upper portion of the syringe, prior to connecting the top portion of the removable non-standard carpule barrel to the upper portion of the syringe.

In still another example embodiment, the syringe needle may be connected to a bottom portion of the non-standard carpule barrel, which is removable or irremovable from the syringe. The connecting of the syringe needle may be removably or irremovably connected to the bottom portion of the non-standard carpule barrel. In an embodiment, the syringe needle may be removably connected to a bottom portion of a removable non-standard carpule barrel, and the removable connection may include threading, screwing, latching, snapping, or combinations thereof. In an alternative embodiment, the syringe needle may be irremovably connected to a bottom portion of a removable non-standard carpule barrel, and the irremovable connection may include welding, bonding, fusing, or combinations thereof.

In an embodiment, a removable non-standard carpule barrel, a non-standard carpule, at least a portion of a syringe, or combinations thereof, may be autoclavable for re-use. In an alternative embodiment, a removable non-standard carpule barrel, a non-standard carpule, at least a portion of a syringe, or combinations thereof, may be disposable after a first or single use.

In an embodiment of the methods for delivering a fluid, the emitting may include emitting, from a non-standard carpule, a greater volume of fluid than the volume of fluid held within a standard carpule. The carpules, themselves, whether standard or non-standard, may include etched or otherwise denoted gradations indicative of units of measurements (e.g., mL, dL, $g/cm^3$ of a certain fluid at a specified temperature also optionally denoted on the carpule along with any other type of indicia). The gradations may be located on the outside, inside, or combinations thereof of the carpule, whether standard or non-standard. By example, marking the carpules with finite units of measurements allows the user of a carpule placed within a syringe, such as those apparatuses described and used in methods disclosed herein, to see, for example, what volume of the fluid is being delivered by depressing a plunger of a syringe to push fluid from the carpule, which may have finite units or gradations of measurements. By reading the gradations, the user may determine the amount of volume that has been dispensed or the amount of volume that remains in the carpule, or any other uses through placement of gradations or indicia on the carpule.

In another embodiment, an apparatus is usable for injection and/or delivery of a fluid, and the apparatus may include a removable non-standard carpule barrel having a top portion, a bottom portion, and a barrel portion therebetween. The top portion may include an opening for receiving a syringe plunger and at least a first portion of a connection mechanism for connecting to an upper portion of the syringe. The bottom portion may include another opening capable of holding a bottom end of a carpule, which may include a standard carpule or a non-standard carpule, both of which may be removable from the syringe. The top portion may be integrally or removably connected to an upper portion of the syringe, and/or the bottom portion may be integrally or removably connected to a syringe needle portion, optionally including the needle of the syringe.

The non-standard barrel portion may be located between the top portion and bottom portion, and the barrel portion may include a cradle. In an embodiment, the cradle may have a length that may be capable of holding a removable standard carpule or a removable non-standard carpule, and the cradle may have a width that may be greater than a standard carpule, which may be removable.

In an embodiment, a removable non-standard carpule barrel may be located in a lower portion of a syringe. In an embodiment, the bottom portion of the syringe may have a convex portion above the another opening, for connecting to a syringe needle portion and/or syringe needle.

In an embodiment, a removable non-standard carpule barrel may include a cradle that may have a width that may be sufficient to hold a volume within a non-standard carpule that is at least twice as large as the volume of a standard carpule. In another embodiment, the cradle may hold a removable non-standard carpule that may have a maximum volume capacity that is smaller than the maximum volume capacity of a standard carpule.

In an embodiment, the top portion of the non-standard carpule barrel may form a removable or irremovable connection with the upper portion of the syringe, and the bottom portion forms a removable or irremovable connection with a syringe needle portion of the syringe.

In an embodiment, at least part of the removable non-standard carpule barrel, the upper portion of the syringe, the lower portion of the syringe, or combinations thereof may be autoclavable for re-use. In an alternative embodiment, at least part of the removable non-standard carpule barrel, the upper portion of the syringe, the lower portion of the syringe, or combinations thereof is disposable after a single or first use.

In an embodiment, the non-standard carpule barrel may be removable or irremovable and may be loaded with removable non-standard carpule that may include an integrated or removable plug for sealing a cavity, such as by inserting into or placing over top of the cavity, which is located at a top end of the non-standard carpule.

In another example embodiment, disclosed is a non-standard carpule barrel, which may include a top portion, which may include an opening for receiving a syringe plunger and at least a first portion of a connection mechanism for connecting to an upper portion of a syringe. Further, disclosed is a bottom portion comprising another opening capable of holding a bottom of a carpule, a section of a syringe needle, or combinations thereof, wherein the carpule comprises a removable standard carpule or a removable non-standard carpule. Further still, disclosed is a barrel portion located between the top portion and the bottom portion, wherein the barrel portion comprises a cradle, wherein the cradle has a length capable of holding the removable standard carpule or the removable non-standard carpule, and a width greater than the removable standard carpule.

In yet another example embodiment, disclosed is a non-standard carpule barrel, which may include a barrel portion located between a top portion and a bottom portion, wherein the barrel portion comprises a cradle, wherein the cradle has a length capable of holding a removable standard carpule or removable non-standard carpule, wherein the removable non-standard carpule has a width greater than the removable standard carpule. The non-standard carpule barrel may also include a guidance bearing located within the barrel portion, the guidance bearing comprising a backer portion having a first end and a second end, wherein an upper portion of the guidance bearing extends through first end.

BRIEF DESCRIPTION OF THE DRAWINGS

So that the manner in which the above recited features, advantages and objects of this disclosure are attained and may be understood in detail, a more particular description, briefly summarized above, may be had by reference to the embodiments thereof which are illustrated in the appended drawings.

It is to be noted, however, that the appended drawings illustrate only typical embodiments of this disclosure and are therefore not to be considered limiting of its scope, for the disclosure may admit to other equally effective embodiments.

DETAILED DESCRIPTION

The following is a detailed description of example embodiments accompanied by drawings. The embodiments are examples and are in such detail as to clearly communicate the claimed invention. However, the amount of detail offered is not intended to limit the anticipated variations of embodiments; on the contrary, the intention is to cover all modifications, equivalents, and alternatives falling within the spirit and scope of the invention as defined by the claims. The detailed descriptions below are designed to make such embodiments obvious to a person of ordinary skill in the art.

In addition, directional terms, such as "above," "below," "upper," "lower," "front," "back," "top," "bottom," etc., are used for convenience in referring to the accompanying drawings. In general, "above," "upper," "upward," "top," and similar terms refer to a direction away the earth's surface, and "below," "lower," "downward," "bottom," and similar terms refer to a direction toward the earth's surface, but is meant for illustrative purposes only, and the terms are not meant to limit the disclosure.

Generally disclosed are methods and apparatuses for transfer of a solution or other fluid to or from a body (e.g., human or non-human patient) by use of a syringe having a carpule, i.e., a standard or non-standard carpule, wherein the latter has a different size, whether smaller or larger, than a standard carpule, which generally holds a 1.8 mL volume of fluid. Henceforth, the transfer of the solution or other fluid discussion continues in terms of delivering a medicine within a non-standard carpule, but, it is understood that the discussion equally applies to withdrawing solution(s) or other fluid(s) from a body, e.g., a human or non-human patient, into the standard or non-standard carpule.

Figure 1:
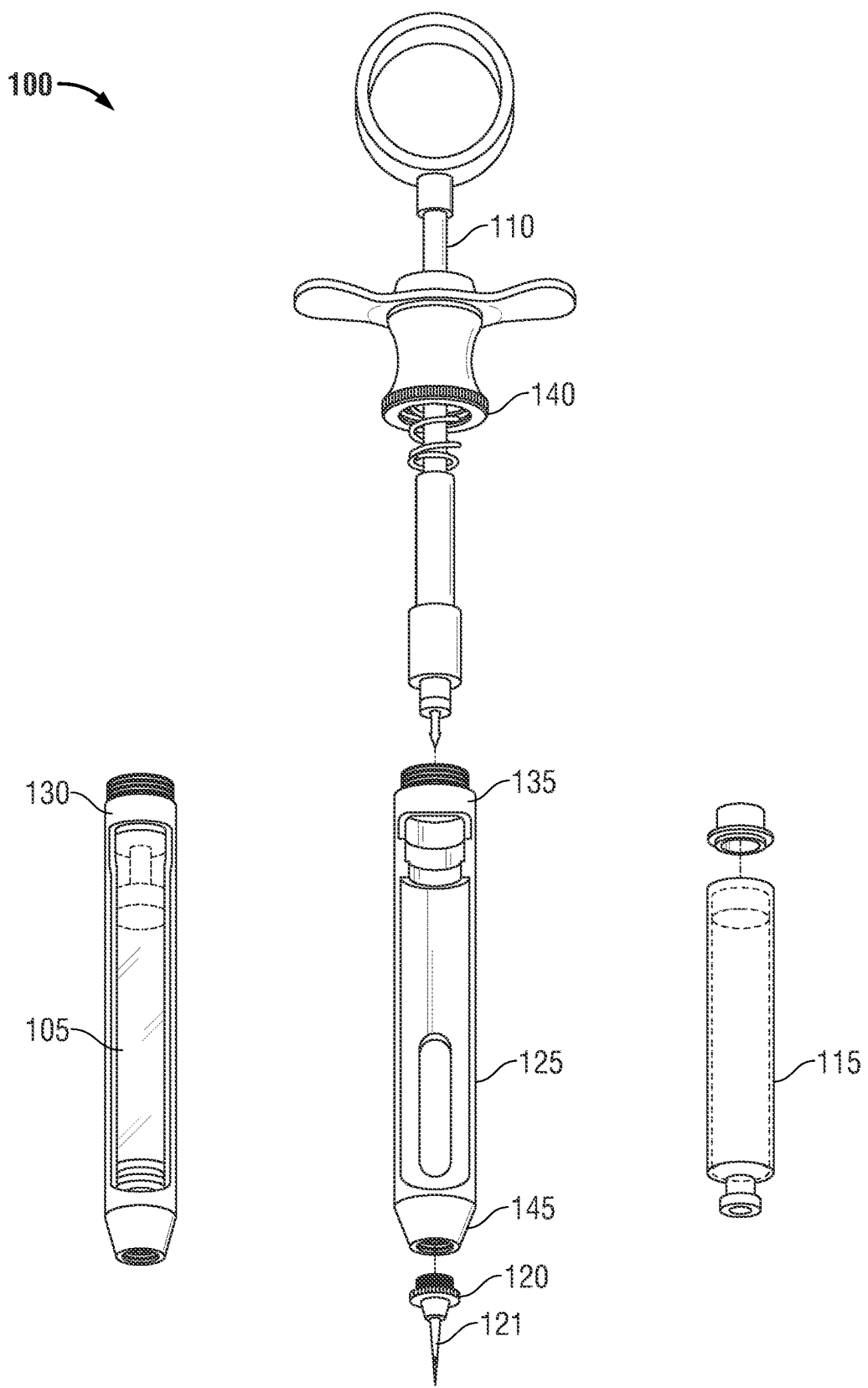
FIG. 1 depicts an exploded view of a syringe, wherein shown are example embodiments of syringe components that include an upper portion having a syringe plunger, a non-standard carpule barrel, a syringe needle portion having a needle, a non-standard carpule, a plug, and a standard carpule loaded in a barrel in accordance with the disclosed methods and apparatuses.

With reference to FIG. 1, disclosed are methods and apparatuses for transferring a fluid, wherein the fluid may be an injectable medicine, solution or other fluid. The method may include applying a force to a syringe plunger 110, to act upon a non-standard carpule 115 loaded into a syringe 100, wherein the non-standard carpule 115 has a volume that is different (i.e., greater or less than) from the volume of fluid contained within a standard carpule 105. If the object, for example, is to decrease the number of shots of medicine to inject into a patient, then the non-standard carpule 115 in the syringe 100 is likely larger than the standard carpule 105, due to the capability of the non-standard carpule 115 to hold a greater volume of medicine. Subsequent to applying the force, the solution in the non-standard carpule 115 may move through the syringe needle 121, located at the bottom of the syringe 100, wherein the syringe needle 121 may be in fluid communication with the non-standard carpule 115 having the fluid, e.g., medicine, solutions, or other fluids. The volume of the fluid in the non-standard carpule 115 may adjust subsequent to the applying of the force and the moving of the solution through the syringe needle 121. In the instance where applying the force involves pushing down on the syringe plunger 110, then the volume of the solution within the non-standard carpule 115 may adjust so as to increase in the volume of the fluid. In the opposite instance where applying the force involves pulling up on the syringe plunger 110, then the volume of the fluid within the non-standard carpule 110 may adjust so as to decrease in the volume of the fluid.

Figure 2:
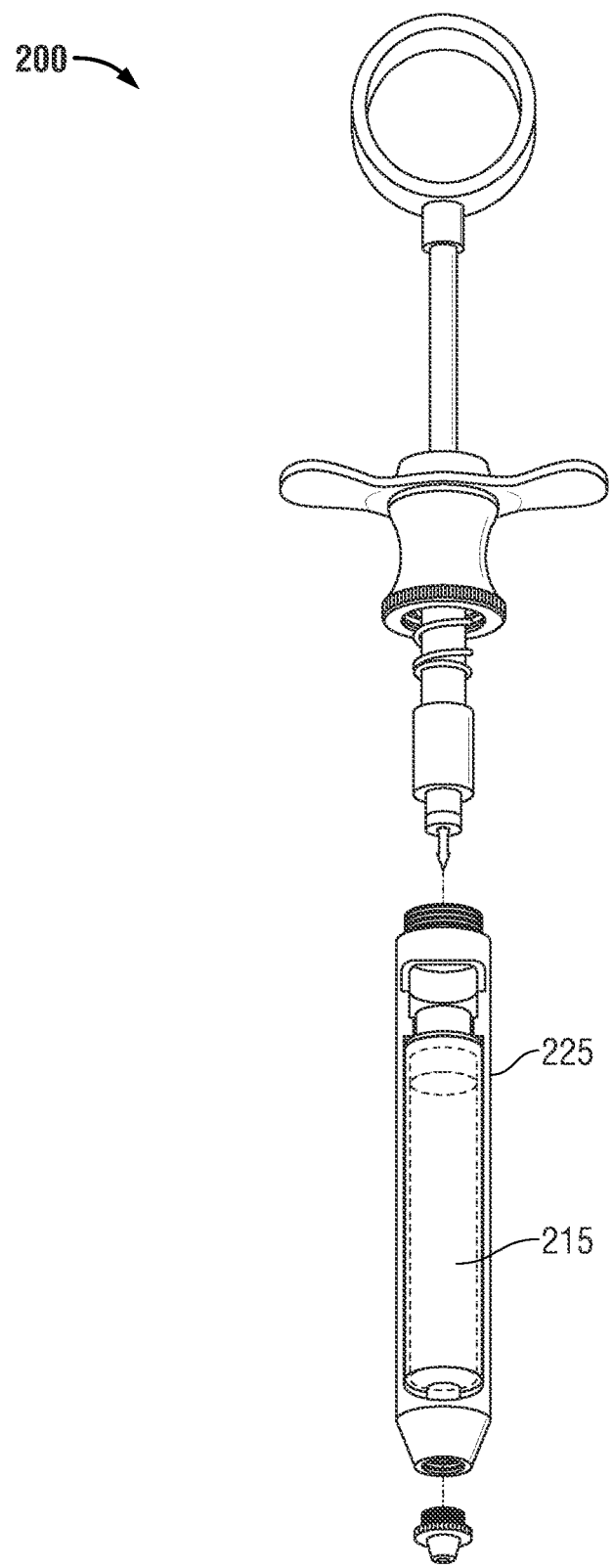
FIG. 2 depicts an example embodiment of a syringe having an upper portion with a syringe plunger separated from a lower portion, which includes a non-standard carpule loaded in a non-standard carpule barrel that is separated from a syringe needle portion in accordance with the disclosed methods and apparatuses.

Embodiments include apparatuses and methods usable for delivering a solution or other fluid from a syringe 100 to a body (e.g., human patient or non-human patient). With reference to FIGS. 1 and 2, the methods may include loading a non-standard carpule 115, 215 into a syringe 100, 200 having a non-standard carpule barrel 125, 225, which may differ in dimensions regarding length, width, size, shape, and/or circumference, as compared to a standard carpule barrel 130. Loading the non-standard carpule or loading the syringe may be understood to mean placing the non-standard carpule 115, 215 within the non-standard carpule barrel 125, 225. As previously discussed and with reference to FIG. 1, the non-standard carpule 115 has a volume that is different from a standard carpule 105. Within the volume of the non-standard carpule may be a fluid, which may comprise a solution of medicine or another substance.

Subsequent to loading the syringe 100 with the non-standard carpule, the methods may include exerting a force on the syringe plunger 110 and pushing down, using the force applied to the syringe plunger 110, on the fluid within the non-standard carpule 115, which may result in emitting the fluid from a needle 121 of the syringe 100, which is in fluid communication with the non-standard carpule 115. When the volume of the fluid within the non-standard carpule 115 is greater than the volume capable of being held by a standard carpule 105, then it follows that the emitting step may result in emitting a greater volume of solution than that which is capable of being held and emitted by a standard carpule 105. The non-standard carpule 115 may or may not be designed to be disposable after a single use. Considerations of disposability may include cost and biodegradability of the material (e.g., inert plastics such as polycarbonates or any type of material) used for constructing the non-standard carpule 115, wherein autoclaving or other sterilizing methods may permit an effective re-use of the non-standard carpule, as well as the syringe, including the non-standard carpule barrel of the syringe.

In returning to FIG. 1, the apparatus and methods may include connecting a top portion 135 of the non-standard carpule barrel 125 to an upper portion 140 of the syringe 100. In alternative example embodiments, the non-standard carpule barrel 125 may be removably connected or non-removably connected to an upper portion 140 of the syringe 100. In the removable case, the connection may be consummated by any known means, such as screwing/unsrewing, snapping/unsnapping, latching/unlatching, or other forms of removable mating or connecting. In the non-removable case, the irremovable connection may be consummated by any known means, such as by injection molding, wherein the upper portion 140 and the non-standard carpule barrel 125 are part of a unified piece of plastic or other moldable material. Other forms, usable for forming a non-removable connection between the top portion 135 of the non-standard carpule barrel 125 and the upper portion 140 of the syringe 100, may include welding, bonding, or fusing the two portions together, as well as other forms of irremovable mating.

Returning to the removable case, the syringe 100 may permit modularity or inter-changeability through use of a removable barrel. That is, prior to removably connecting the non-standard carpule barrel 125 to the upper portion 140 of the syringe 100, it may be necessary to remove a barrel already connected to the upper portion 140 of the syringe 100. Such inter-changeability or modularity may comprise exchanging one non-standard carpule barrel for another non-standard carpule barrel or for a standard carpule barrel.

Similarly, the disclosed methods and apparatuses may include connecting the needle 121 of the syringe 100, such as through a syringe needle portion 120, to a bottom portion 145 of the non-standard carpule barrel 125. In the removable case, the connection may be consummated by any known means, such as screwing/unscrewing, snapping/unsnapping, latching/unlatching, or other forms of removable mating and/or connecting. In the non-removable case, the irremovable or permanent connection may be consummated by any known means, such as by injection molding, wherein the bottom portion 145 and the non-standard carpule barrel 125 are part of a unified piece of plastic or other moldable material. Other forms, usable for forming a non-removable connection between the bottom portion 140 of the non-standard carpule barrel 125 and the syringe needle portion 120, may include welding, bonding, or fusing the two portions together, as well as other forms of irremovable mating.

In view of the removable and irremovable components of the syringe 100 disclosed herein, the disclosed apparatus and methods may permit all or part of the syringe 100, such as the non-standard carpule barrel 125, the non-standard carpule 115, or combinations thereof, and so forth to be made of materials capable of being autoclaved.

Figure 3A:
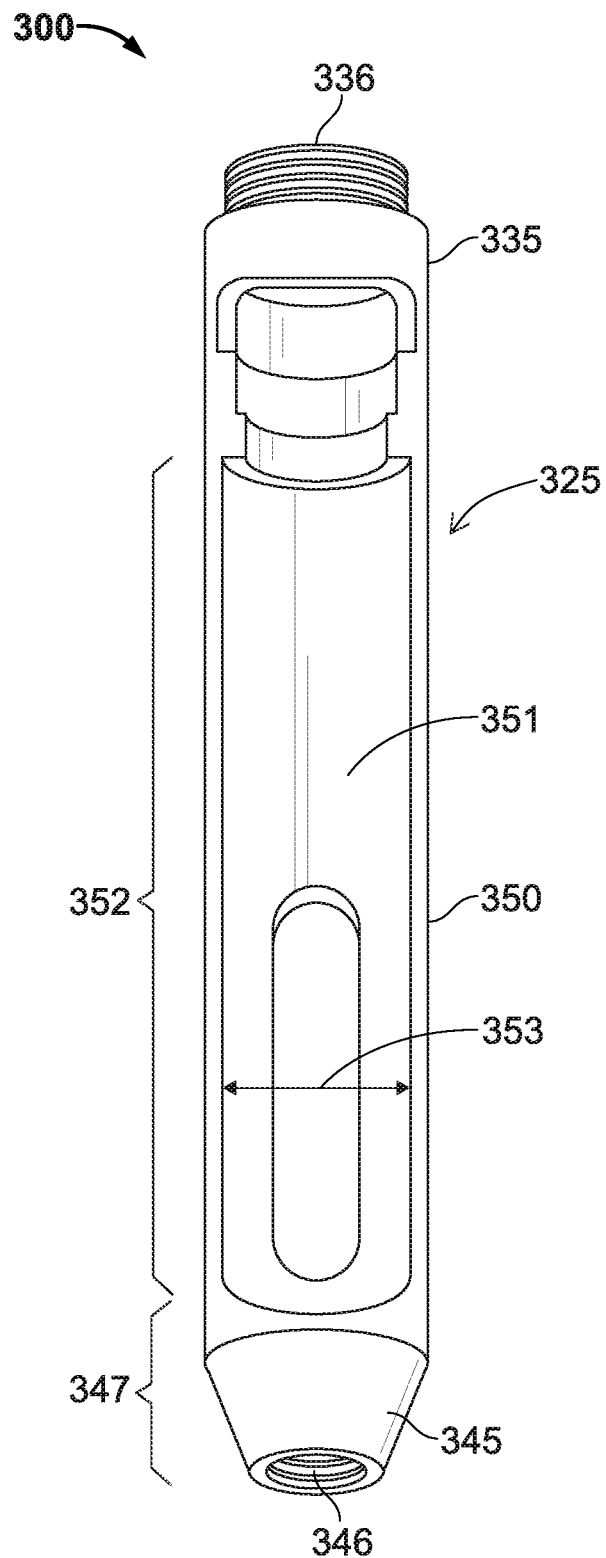
FIG. 3B depicts an example embodiment of a non-standard carpule having a plug in its cavity alongside FIG. 3A, which depicts a non-standard carpule barrel in accordance with the disclosed methods and apparatuses.

With reference to FIG. 3A, further discussion of the non-standard carpule barrel 325 now ensues. The non-standard carpule barrel 325, may be interchangeable (removable) and may constitute the lower portion 300 of the syringe (100 in FIG. 1), alongside an optional connection to a syringe needle (121 in FIG. 1). The non-standard carpule barrel 325 may include a top portion 335, a bottom portion 345, and a barrel portion 350 therebetween. As shown, the top portion 335 may include an opening 336 for receiving a syringe plunger (110 in FIG. 1), and at least a first portion of a connection mechanism for connecting to an upper portion (140 in FIG. 1) of the syringe (100 in FIG. 1). In an embodiment, the first portion of the connection mechanism may include threading, a latch, a snap, a weld, or other removable components or mechanisms for consummating a removable connection with the upper portion (140 in FIG. 1) of the syringe 100, as previously discussed. As such, the upper portion (140 in FIG. 1) of the syringe (100 in FIG. 1) may connect to a complimentary and removably connectable second portion (i.e., the first portion of the connection mechanism) for consummating a removable connection between the upper portion (140 in FIG. 1) of the syringe and the top portion 335 of the non-standard carpule barrel 325. In an alternative embodiment, the first portion of the connection mechanism of the top portion 335 may form a non-removable or permanent connection with the upper portion (140 in FIG. 1) of the syringe (100 in FIG. 1), such that the upper portion (140 in FIG. 1) of the syringe (100 in FIG. 1) connects to the top of the non-standard carpule barrel 325, and there are no separate sections of the non-standard carpule barrel 325, such that the joined upper portion (140 in FIG. 1) and lower portion 300 of the syringe form a continuous syringe structure.

Figure 3B:
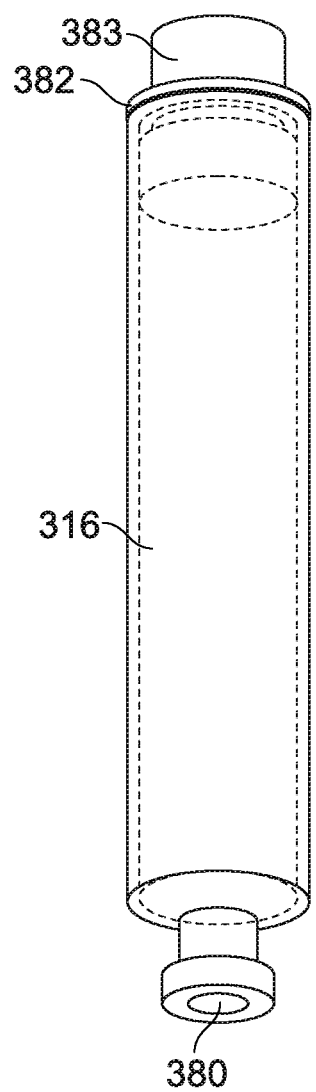

As shown in FIG. 3A, the bottom portion 345 of the non-standard carpule barrel 325 includes another opening 346 that may be capable of holding a bottom end 380 of a carpule, which may be a standard carpule (105 in FIG. 1) or a non-standard carpule 316. The barrel portion 350 of the non-standard carpule barrel 325 is shown in FIG. 3B and is located between the top portion 335 and the bottom portion 345, wherein the barrel portion 350 may comprise a cradle 351 for holding the carpule. The cradle 351 may have a length 352 for holding a standard or non-standard carpule and a width 353 that may hold the standard carpule, or a width for holding a non-standard carpule that is greater than the width required for holding the standard carpule (105 in FIG. 1). A point to be made here is that, for example, the non-standard carpule barrel 325 may hold a non-standard carpule 316 that has the same length as a standard carpule (105 in FIG. 1), but a different width as compared to a standard carpule (105 in FIG. 1), wherein the different width, for example, may be wider so that a greater volume of fluid may be delivered through a single use of a carpule-loaded syringe.

Similar to the foregoing discussion of the top portion 335 having a connection mechanism for connecting to an upper portion (140 in FIG. 1) of the syringe (100 in FIG. 1), the same connectability discussion may be applied to the bottom portion 345. That is, in an embodiment, the bottom portion 345 may comprise a connection mechanism at its opening 346, which may be threaded, latched, snapped, welded, or removably connected by any other means, for connecting to the syringe needle portion (120 of FIG. 1). In an alternative embodiment, the connection mechanism may be irremovably or permanently connected with syringe needle portion (120 in FIG. 1), forming one continuous syringe structure. Further, the syringe needle (121 in FIG. 1) may be removably or irremovably connected with the syringe needle portion (120 in FIG. 1).

The bottom portion 345 of the non-standard carpule barrel 325 may include a convex portion 347 located above the another opening 346. The convexity may aid in holding the loaded carpule within the non-standard carpule barrel 325. As discussed above, the width 353 of the cradle 351 may be wide enough to hold a non-standard carpule, having the added limitation in this case that the non-standard carpule is larger (e.g., wider) than the standard carpule. For example, in such an instance, the non-standard carpule may be at least twice as large as a standard carpule. In another example embodiment, the cradle 351 may hold a non-standard carpule having a maximum volume capacity that is smaller than the maximum volume capacity of a standard carpule. The non-standard carpule, itself, may have a tapered bottom end 380 and a top end 382, wherein the top end 382 has a sealable cavity, wherein the sealing may be accomplished by an optionally integrated or removable plug 383, such as one made from rubber, plastic, or other material, that inserts into or covers over the top end 382. The plug 383 may assist in holding the loaded carpule within the non-standard carpule barrel 325. The plug 383 may seal a cavity, such as by inserting into or placing over top of the cavity, which is located at a top end 382 of the non-standard carpule barrel 325. In other, non-depicted, example embodiments, neither or both of the bottom and top ends are tapered.

Figure 4A:
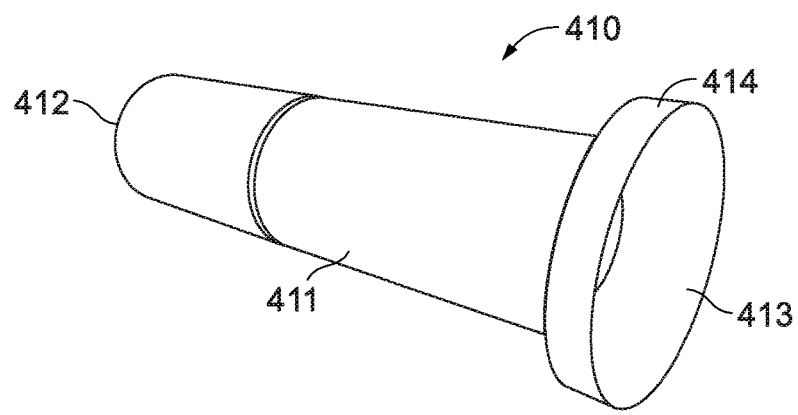
FIGS. 4A-4C depict example embodiments of a removable or irremovable (e.g., integrated) bottom portion and a guidance bearing located near a top end of the lower portion of the non-standard carpule barrel, wherein the guidance bearing includes a backer portion, optionally tapered and therefore having an optionally constant or variable inner diameter, whereby the backer portion may be in communication with a spring that is partially seen beginning in FIGS. 1 and 2, but otherwise is not more visibly depicted, wherein the spring is located between one end of the backer portion and a bottom of the top portion that removably or irremovably mates with the top end of the bottom portion, wherein the one end of the backer portion may have at least a partial interface or other surface on which spring action from application of the plunger may transfer pressure to push down on the backer portion, and the other end of the backer portion pushes down on a standard or non-standard carpule optionally loaded into the non-standard carpule barrel, such that the guidance bearing, optionally having a locking mechanism to fix location(s) of the depressed plunger and consequent delivery of fluid from the carpule through the syringe needle, provides additional guidance of delivery of the solution from the carpule in a syringe apparatus, and the spring may optionally attach to or near the one end of the backer portion in order to permit in tandem recoiling of the spring and guidance bearing upon pulling up on the syringe plunger in accordance with the disclosed methods and apparatuses.
Figure 4B:
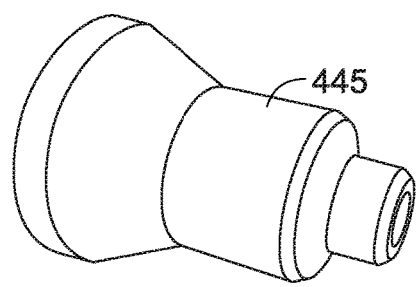
Figure 4C:
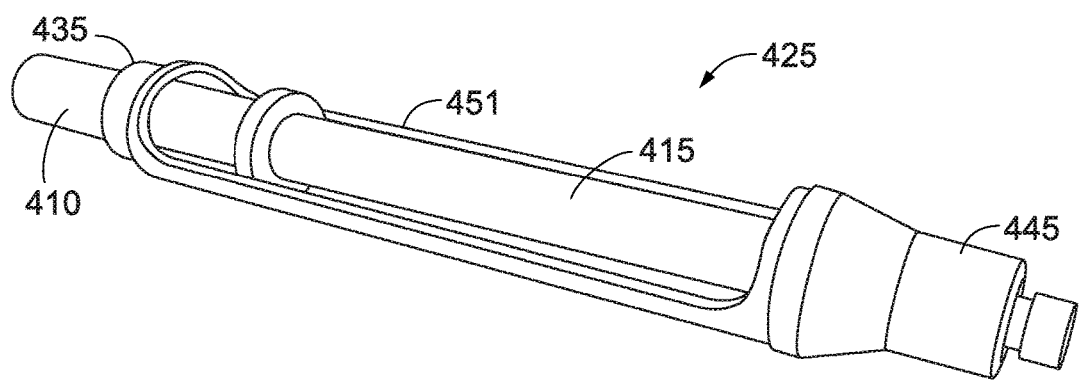

Moving on to FIGS. 4A-4C, disclosed are additional, example embodiments for methods and apparatuses including a guidance bearing 410 into a non-standard carpule barrel 425, which may receive a carpule 415, whether standard or non-standard, in accordance with the methods and apparatuses, such as those disclosed elsewhere herein. A guidance bearing 410 may include a backer portion 411, which is removably or irremovably placed within the non-standard carpule barrel 425, at least partially surrounded and optionally supported by one or more portions of the cradle 451. A first end 412 of the backer portion 411 is located near the top portion 435 of the non-standard carpule barrel 425 and the second end 413 of the backer portion terminates beneath the top portion 435 of the non-standard carpule barrel 425 so as to leave space for the placement of a carpule, whether standard or non-standard, into the non-standard carpule barrel 425.

In further example embodiments, the first end 412 of the backer portion 411 may have an inner diameter that is the same or smaller as compared to the inner diameter located toward or at the end of the second end 413. For example, the backer portion 411 may have an inner diameter at first end 412, whereby the inner diameter gradually increases, whether uniformly or non-uniformly, so that the second end 413 has a greater inner diameter as compared to the inner diameter at the first end 412, and possibly anywhere else in between, or not, these ends 412, 413. The backer portion 411, itself, like other part so the apparatuses discussed herein, may be made of surgical steel, inert plastics, autoclavable materials, or otherwise. Additionally and alternatively, the disposable or non-disposable material(s) molded, tooled or otherwise manufactured in one or multiple modular components—just like any parts or portions of materials used in the disclosed apparatuses herein—for render the backer portion 411 to have an interior that is solid, hollow, or combinations thereof. For instance, the backer portion 411 may have thin walls with a hollow interior, or, in other example embodiments, the backer portion 411 may have an interior diameter that is made of material, such as galvanized aluminum, that runs from one side of backer portion 411 to side directly opposite of the backer portion 411 and from the first end 412 to the second 413 so that the backer portion 411 is one solid piece of galvanized aluminum in shape desired for the backer portion 411.

In other example embodiments, such as particularly shown in FIGS. 4A-4C, the backer portion 411 optionally includes a cap portion 414 located at the second end 413. The cap portion 414 provides yet additional guidance over that discussed, such as in the preceding paragraph, in delivering fluids within a carpule, which is placed beneath the backer portion 411 having such cap portion 414 and is located within the non-standard carpule barrel 425. For instance, the cap portion 414 may enhance stability and mitigate against wobble of the standard carpule or the non-standard carpule during delivery of the fluid.

In further embodiments, the backer portion 411 may move up and down within the non-standard carpule barrel 425, optionally loaded with a standard or non-standard carpule containing medicine, for example, to be delivered to a recipient, by applying force to a syringe plunger, as previously disclosed herein. This movement up and down by the backer portion 411—optionally coupled with minimal torsional movement that may be mitigated by sides of the cradle that optionally flank at least a portion of opposite sides of the backer portion 411—may be added by a non-depicted, spring(s) located above the first end 412 of the backer portion 411, wherein the top of the first end 412 is optionally sealed or otherwise in order to form at least a partial interface on which the spring(s) may push down subsequent to application of force to a syringe plunger in mechanical communication therewith. Upon pulling up on the syringe, the one or more springs recoil, and if said spring(s) is latched or otherwise attached, or even non-attached, such as, merely touching, to said at least a partial interface on a top of the first end 412, then the backer portion 411 recoils in tandem with such spring(s) recoiling. The spring(s) may be attachably or non-attachably connected to at least a partial interface associated with the first end 412 in order to transfer force during movement of a syringe plunger in communication with the spring(s)

FIGS. 4A-4C also depict an example embodiment of a removable or irremovable (e.g., integrated) bottom portion 445 of the non-standard carpule barrel 425 and for its 445 threaded, slide-on, snap-on, or otherwise mating thereto 425 in accordance with disclosed methods and apparatuses herein.

Figure 5A:
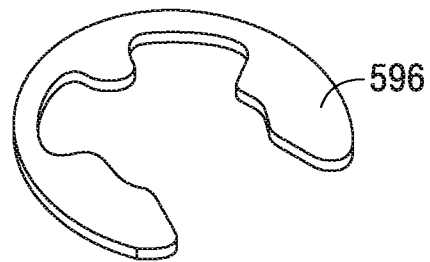
FIGS. 5A-5C depict example embodiments of an optional retaining ring having a diameter "A" for placement within an embellishment of an upper portion of the guidance bearing, whereby the upper portion may jut through the top portion of the non-standard carpule barrel, wherein the top portion may be proximal to an opening that optionally mates with a different upper portion, such as the one depicted in FIG. 1, and in accordance with the disclosed methods and apparatuses.
Figure 5B:
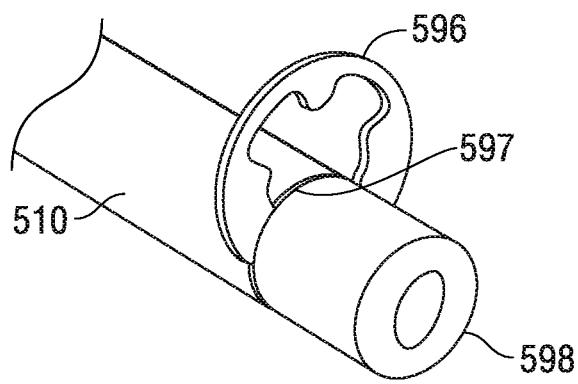
Figure 5C:
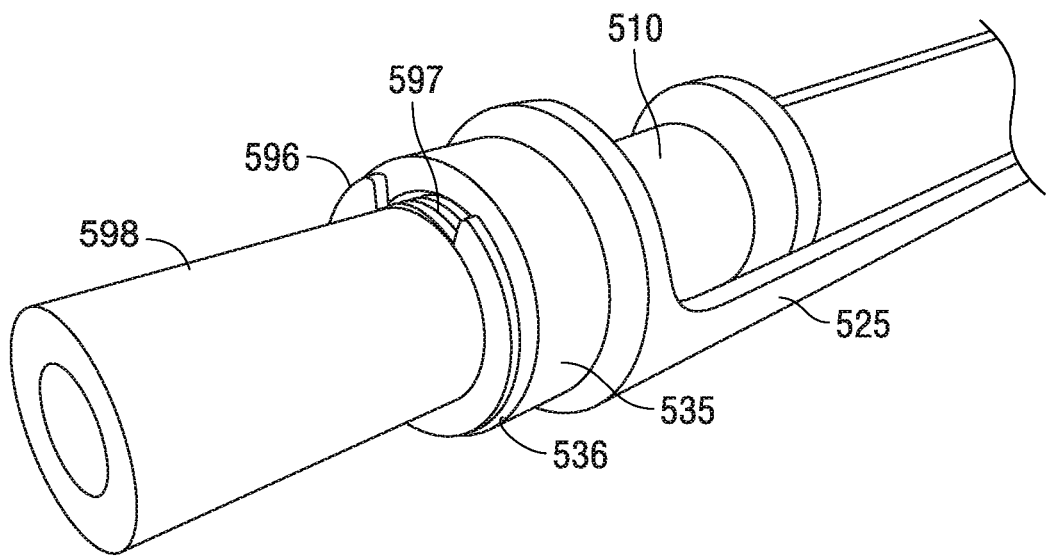

Turning now to FIGS. 5A and 5B, depicted is an example embodiment of an optional retaining ring 596 for placement within an optional embellishment 597 located on or within an upper portion 598 of the guidance bearing 510. In one example such as that depicted in FIGS. 5A and 5B, the guidance bearing 510 has an upper portion 598 that juts through the top portion 535 of the non-standard carpule barrel 525, wherein the top portion 535 may be proximal to an threaded opening 536 (e.g., 336 in FIG. 3A) for optional mating with another upper portion, such as 140 in FIG. 1. In other example embodiments, threaded opening 536 may use other mechanisms as opposed to threading for mating in order to perform the methods and/or form the syringe described in this disclosure. Returning to the upper portion 598 of the guidance bearing 510, disclosed is a groove, raised surface, or other embellishment 597, regardless whether the groove, raised surface, or other embellishment is relatively shallow, deep, high, raised, uniform, non-uniform, etc. In the depicted, example embodiment, a retaining ring 596 may be placed within the embellishment 597 to retain the guidance bearing 510 in its position with respect, for example, to the remainder of previously disclosed apparatuses. e.g., 100, 200, 300. In FIGS. 5A and 5B, retaining ring 596 is shown to have a particular diameter represented by "A," which at least partially circumscribes an upper portion 598 of the guidance bearing 510.

While the foregoing is directed to example embodiments, other and further embodiments may be devised without departing from the basic scope thereof, and the scope thereof is determined by the claims that follow.

What is claimed is:

1. A non-standard carpule barrel comprising:
a barrel portion located between a top and a bottom of the non-standard carpule barrel, wherein the barrel portion comprises a cradle having a length capable of holding a standard carpule or non-standard carpule, wherein the non-standard carpule has a width greater than the standard carpule; and
a guidance bearing located within the barrel portion and configured to receive an upper end of the standard carpule or non-standard carpule, wherein the guidance bearing comprises a first end and a second end, wherein an upper portion of the guidance bearing extends through the top of the barrel portion, a lower portion of the guidance bearing is below the top of the barrel portion, and all of an outer surface of the lower portion extending from the top of the non-standard carpule barrel of the barrel portion to the second end of the guidance bearing is exposed to an inner surface of the barrel portion, and wherein an outer surface of the second end of the guidance bearing contacts an inner surface of the barrel portion.

2. The non-standard carpule barrel of claim 1, wherein the guidance bearing is removable from the barrel portion.

3. The non-standard carpule barrel of claim 1, wherein the guidance bearing is at least partially surrounded and supported by one or more portions of the cradle.

4. The non-standard carpule barrel of claim 1, wherein the first end of the guidance bearing is located at least partially above the top of the barrel portion and the second end of the backer portion is located at least partially beneath the top of the barrel portion of the non-standard carpule barrel.

5. The non-standard carpule barrel of claim 4, further comprising a space beneath the second end of the guidance bearing for placement of the standard carpule or the non-standard carpule within the cradle of the barrel portion.

6. The non-standard carpule barrel of claim 1, wherein the guidance bearing has a uniform inner diameter.

7. The non-standard carpule barrel of claim 1, wherein the guidance bearing comprises one or more shape-formable materials, and wherein the guidance bearing is hollow.

8. The non-standard carpule barrel of claim 1, further comprising one or more springs connected to at least a partial interface associated with the first end of the guidance bearing to transfer force during movement of a syringe plunger in communication with the one or more springs.

9. The non-standard carpule barrel of claim 1, further comprising one or more embellishments located on or within the upper portion of the guidance bearing that extends beyond the top of the barrel portion.

10. The non-standard carpule barrel of claim 9, further comprising one or more retaining rings located within the one or more embellishments located on or within the upper portion of the guidance bearing for retaining movement.

11. The non-standard carpule barrel of claim 1, wherein the standard carpule and the non-standard carpule are interchangeable.

12. The non-standard carpule barrel of claim 1, wherein the guidance bearing has a conical shape.

13. A method for delivering a fluid, the method comprising: loading a standard carpule or a non-standard carpule, beneath a second end of a guidance bearing located within a barrel portion of a non-standard carpule barrel of a syringe, the second end of the guidance bearing being provided below a top of the barrel portion so that all of an outer surface of the second end extending from the top of the barrel portion to the second end of the guidance bearing is exposed to an inner surface of the barrel portion, and so that an outer surface of the second end of the guidance bearing contacts an inner surface of the barrel portion, wherein the syringe further comprises a syringe plunger and a syringe needle, and wherein the non-standard carpule has a volume of fluid that is greater than the volume of the fluid within the standard carpule;
applying a force to the syringe plunger to push the volume of the fluid within the standard carpule or the non-standard carpule towards the syringe needle;
emitting at least a portion of the volume of the fluid from the syringe needle in fluid communication with the standard carpule or the non-standard carpule; and
guiding the loading, applying, and emitting via the guidance bearing.

14. The method of claim 13, further comprising retaining the guidance bearing in position through one or more retainer rings placed within one or more embellishments located on or within an upper portion of the guidance bearing.

15. The method of claim 13, wherein the applying comprises transferring the force via one or more springs connected to at least a partial interface associated with a first end of the guidance bearing.

16. The method of claim 13, wherein the second end of the guidance bearing comprises is a cap portion, wherein the cap portion mitigates wobble of the standard carpule or the non-standard carpule during delivery of the fluid.

17. The method of claim 13, wherein the guidance bearing has a conical shape.

* * * * *